US009192323B2

(12) United States Patent
Heyer et al.

(10) Patent No.: US 9,192,323 B2
(45) Date of Patent: Nov. 24, 2015

(54) SYSTEM FOR DETECTING RESPIRATORY MUSCLE ACTIVITY OF A PATIENT RECEIVING ASSISTED BREATHING

(75) Inventors: Laurent Heyer, Paris (FR); Pierre Baconnier, Grenoble (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 394 days.

(21) Appl. No.: 13/127,187

(22) PCT Filed: Nov. 3, 2009

(86) PCT No.: PCT/FR2009/052119
§ 371 (c)(1),
(2), (4) Date: Jul. 18, 2011

(87) PCT Pub. No.: WO2010/061091
PCT Pub. Date: Jun. 3, 2010

(65) Prior Publication Data
US 2011/0263998 A1     Oct. 27, 2011

(30) Foreign Application Priority Data
Nov. 3, 2008    (FR) ...................................... 08 57452

(51) Int. Cl.
*A61B 5/08*       (2006.01)
*A61B 5/087*      (2006.01)
*A61M 16/00*     (2006.01)

(52) U.S. Cl.
CPC . *A61B 5/08* (2013.01); *A61B 5/087* (2013.01); *A61M 16/0051* (2013.01); *A61M 2016/0027* (2013.01); *A61M 2016/0036* (2013.01); *A61M 2230/40* (2013.01)

(58) Field of Classification Search
CPC .......... A61B 5/224; A61B 5/08; A61B 5/087; A61B 5/0871; A61B 5/0873; A61B 5/0875; A61B 5/0876; A61B 5/0878; A61B 5/09
USPC .................................................. 600/529–543
See application file for complete search history.

(56) References Cited

U.S. PATENT DOCUMENTS 5,316,009 A  *   5/1994   Yamada ........................ 600/533
2003/0045807 A1    3/2003   Daniels, II et al.
(Continued)

FOREIGN PATENT DOCUMENTS

EP            1421902        5/2004

OTHER PUBLICATIONS

Heyer, Laurent, et al. "Non-invasive detection of respiratory muscles activity during assisted ventilation." Comptes Rendus Biologies 325.4 (2002): 383-391.*
(Continued)

*Primary Examiner* — Navin Natnithithadha
*Assistant Examiner* — Meredith Weare
(74) *Attorney, Agent, or Firm* — Blank Rome LLP

(57) ABSTRACT

The invention relates to a system for detecting respiratory muscle activity of a patient (1) receiving assisted breathing, which is connected to an assistance device (2) by a pneumatic circuit (3). Said system is characterised in that it comprises: a means (4, 5) for acquiring air pressure and flow signals in the pneumatic circuit (3), sent to a means (6) for continuously estimating the theoretical air pressure expected in the pneumatic circuit in absence of respiratory muscle activity from the patient; and a means (7) for comparing estimated and actual theoretical pressures in order to continuously detect a pressure differential showing respiratory muscle activity in the patient.

7 Claims, 1 Drawing Sheet

(56) References Cited

U.S. PATENT DOCUMENTS

2003/0159695 A1* 8/2003 Younes .................. 128/204.18
2004/0040560 A1    3/2004 Euliano et al.
2011/0301481 A1* 12/2011 Heyer et al. .................. 600/529

OTHER PUBLICATIONS

Engeman, Richard M., George D. Swanson, and Richard H. Jones. "Input design for model discrimination: application to respiratory control during exercise." Biomedical Engineering, IEEE Transactions on 10 (1979): 579-585.*

Yamada et al. "Respiratory muscle pressure analysis in pressure-support ventilation." J Appl Physiol (1985). Nov. 1994;77(5):2237-43.*

Guttmann et al. "Maneuver-free determination of compliance and resistance in ventilated ARDS patients." Chest. Oct. 1992;102(4):1235-42.*

* cited by examiner

SYSTEM FOR DETECTING RESPIRATORY MUSCLE ACTIVITY OF A PATIENT RECEIVING ASSISTED BREATHING

CROSS-REFERENCE TO PRIOR APPLICATIONS

This application is a U.S. National Phase application under 35 U.S.C. §371 of International Application No. PCT/FR2009/052119, filed on Nov. 3, 2009 and claims benefit of priority to French Patent Application No. 0857452, filed on Nov. 3, 2008. The International Application was published in French on Jun. 3, 2010 as WO 2010/061091 A1 under PCT Article 21(2). All of these application are herein incorporated by reference.

The present invention relates to a system for detecting respiratory muscle activity of a patient receiving assisted breathing and who is connected to a corresponding assistance apparatus via a pneumatic circuit.

This system falls within the scope of research on the optimization of strategies and methods for monitoring and assisting with the respiratory function in anesthesia and resuscitation.

Advancements in anesthesia and resuscitation aim to reduce the duration of monitoring and assistance of the quality of the patient's recovery.

Respiratory assistance must ensure effective and non-harmful ventilation with acceptable patient comfort.

In this context, the agreement between a patient and the corresponding respiratory device is key. In a clinical situation, the detection of any disagreement is crucial to optimize the therapeutic strategy.

In the state of the art, monitoring of the interaction between the patient and his assistance apparatus is faced with the difficulty of correctly estimating the patient's respiratory activity in a robust and non-invasive manner.

Indeed, current non-invasive devices are regularly subject to defects. The limitations of these devices, which are currently used in assistance apparatuses, are responsible for a lack of detection of inhalation by the patient, which causes a disagreement between the patient and the assistance apparatus and results in less than optimal assistance.

The alternative devices currently available in the state of the art require sensors measuring the muscular respiratory activity that are both invasive (intrathoracic pressure, needle electromyography . . . ) and not very robust either due to physiological disruptions or the patient's clinical evolution, or due to the lifetime of the sensor to ensure continuous monitoring.

The invention therefore aims to resolve these problems.

To that end, the invention relates to a system for detecting respiratory muscle activity of a patient receiving assisted breathing, which is connected to an assistance apparatus by a pneumatic circuit, characterized in that it comprises:
- a means for acquiring air pressure and flow signals in the pneumatic circuit, sent to a means for continuously estimating the theoretical air pressure expected in the pneumatic circuit in absence of respiratory muscle activity from the patient, and
- a means for comparing estimated and actual theoretical pressures in order to continuously detect a pressure differential showing respiratory muscle activity in the patient.

According to other aspects of the invention, the system for detecting the respiratory muscle activity of a patient receiving respiratory assistance comprises one or several of the following features:
- the estimating means comprises configurable and adaptive means for modeling the patient's passive respiratory system;
- the modeling means assumes the form of models depending at least on the air volume and flow circulating in the pneumatic circuit,
- the modeling means comprises a set of configurable models and in that the estimating means comprises a means for extracting, from the measured pressure signal, input parameters for said models, so as to trigger the operation of these models based on these parameters and a means for selecting the most discriminating model in terms of detection and non-detection of respiratory muscle activity by the patient and/or the simplest in terms of number of parameters used, to make its estimate,
- the means for extracting parameters is adapted to extract the parameters over at least one mechanical cycle made up successively of an inflation and an exhale, excluding the pressurization phase at the beginning of the mechanical cycle in progress and the phase triggering the inflation for the following cycle, at the end of the mechanical cycle in progress,
- the pressurization phase and the phase triggering the inflation are detected by a means for analyzing the air pressure and flow in the pneumatic circuit,
- the analysis means is connected to the means for acquiring pressure and flow signals in the pneumatic circuit,
- the analysis means is integrated into the assistance apparatus,
- the pressurization and inflation triggering phases are detected by an analysis means from a complementary signal delivering physiological information related to the patient's respiratory muscle activity, and
- the complementary signal is a surface electromyogram signal, Thus, a system according to the invention makes it possible to ensure detection of the respiratory muscle activity of a patient receiving assisted breathing, on one hand from non-invasive measurements already available most of the time with current respiratory assistance apparatuses, and on the other hand with a method that makes it possible to bypass the limitations related to the evolution of the patient's clinical state, from already known methods.

The invention will be better understood upon reading the following description, which is provided solely as an example and is done in reference to the appended drawings, in which.

The system according to the invention is based on a detection/adaptive calculation of a muscle pressure representative of the respiratory muscle activity of a patient receiving assisted breathing.

The muscle pressure can be detected or calculated from flow and pressure signals measured in the pneumatic circuit connecting the patient to the assistance apparatus, In each mechanical cycle, the parameters of a mechanical model of the patient's passive respiratory system are identified on predetermined ranges of the breathing cycle from the flow signal in order to estimate, over the entire mechanical signal, the expected theoretical pressure in the absence of muscle activity by the patient. The arithmetic difference between this theoretical pressure and the measured pressure is representative of the pressure generated by the patient's respiratory muscle activity and is called muscle pressure (Pmus). The zero deviation of this pressure indicates a respiratory muscle activity involving inhalation or exhalation depending on the sign of the deviation. In this way, the patient's breathing cycles are identified, a breathing cycle including a complete exhalation and inhalation.

Owing to such a system, it is possible to automatically adapt the parameters for calculating the muscle pressure both to the mechanical specificities of the patient's passive respiratory system and the particularities of the respiratory behavior so that the detection of the respiratory muscle activity is continuously as optimal as possible.

This system uses the knowledge about the conditions for triggering inflations to adapt the parameters for calculating the muscle pressure, the choice of the mechanical model of the passive respiratory system, the definition of zones for identifying parameters of this model, and the choice of thresholds for detecting muscle activity during the mechanical cycle.

Figure 1:
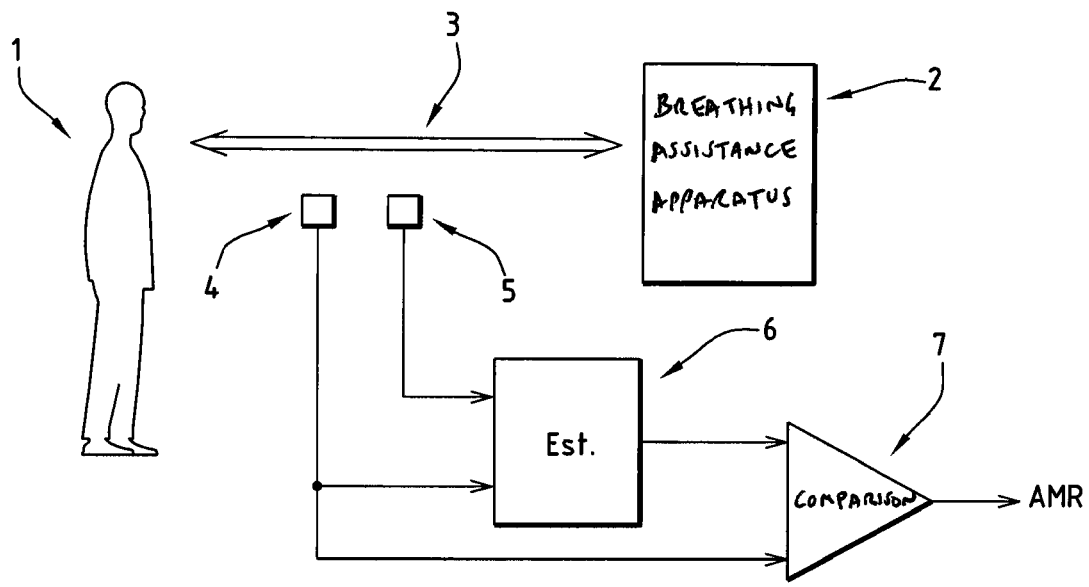
FIG. 1 shows a synoptic diagram illustrating the structure and operation of a detection system according to the invention.

Such a system is diagrammatically illustrated FIG. 1.

In FIG. 1, the patient is designated by general reference 1 and the breathing assistance apparatus is designated by general reference 2, the patient and the respiratory apparatus being connected by a pneumatic circuit designated by general reference 3, traditionally.

In the embodiment illustrated in this figure, the pneumatic circuit 3 is connected to means for acquiring air pressure and flow signals in this circuit, these means being designated by references 4 and 5, respectively.

These acquisition means 4 and 5 are then adapted to deliver these signals to a means for continuously estimating the theoretical pressure of the air anticipated in the pneumatic circuit in the absence of respiratory muscle activity by the patient.

This estimating means is designated by general reference 6 in FIG. 1 and is based on the use of configurable and adaptive means for modeling the patient's passive respiratory system, as will be described in more detail below.

This estimating means 6 then delivers estimated theoretical pressure information to the comparison means designated by general reference 7, receiving, in another input, the pressure actually measured in the pneumatic circuit, which enables continuous detection of a pressure differential representative of the patient's respiratory muscle activity.

In fact, and as previously indicated, the arithmetic differential between this estimated theoretical pressure and the measured pressure is representative of the pressure generated by the patient's respiratory muscle activity and is called muscle pressure Pmus. The zero deviation of this pressure indicates a respiratory muscle activity involving inhalation or exhalation depending on the sign of the deviation.

Figure 2:
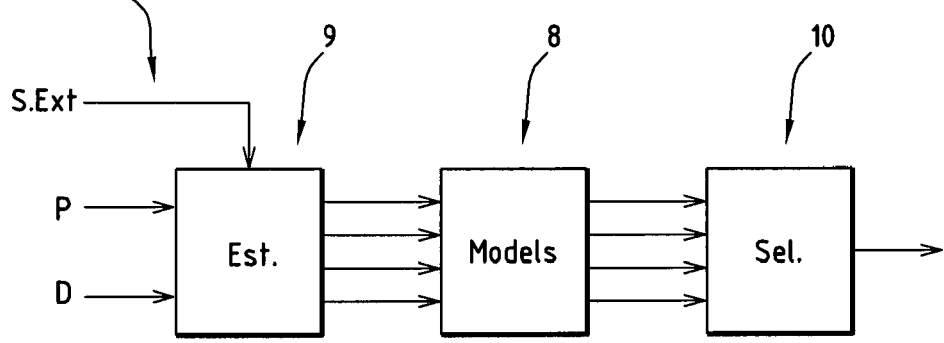
FIG. 2 shows a synoptic diagram illustrating the structure and operation of a pressure estimating means included in the composition of a system according to the invention.

As illustrated in FIG. 2, the means for modeling the estimating means comprises a set of configurable models of patient passive respiratory systems, designated by general reference 8 in that figure. Such models are already well known in the state of the art and make it possible to model the mechanical behavior of the patient's respiratory system, as will be described in more detail below.

These models are configurable, and the estimating means then comprise a means for extracting, from the measured pressure signal, input parameters for these models on as to trigger the operation of said models based on those parameters. This extraction means is designated by general reference 9 in FIG. 2, and the operation thereof will also be described in more detail below.

The estimating means 6 also comprises means for selecting the most discriminating model in terms of detection and non-detection of the patient's respiratory muscle activity and/or the simplest in terms of number of parameters used, to make its estimate, this selection means being designated by general reference 10.

Figure 3:
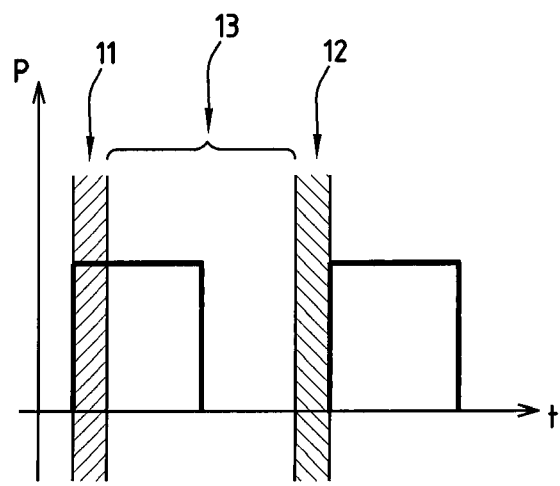
FIG. 3 illustrates a mechanical inflation and exhalation cycle.

In fact, and as illustrated for example in FIG. 3, the means 9 for extracting parameters is adapted to extract the parameters from at least one mechanical cycle successively made up of an inflation and an exhalation, for example by excluding the pressurization phase at the beginning of the mechanical cycle in progress and the phase triggering the inflation of the following cycle, at the end of the mechanical cycle in progress.

This is illustrated by the shaded areas in FIG. 3, where successive mechanical cycles are shown. The shaded area designated by general reference 11 in this FIG. 3 corresponds to the pressurization phase at the beginning of the mechanical cycle in progress, while the shaded area designated by general reference 12 corresponds to the phase for triggering the inflation of the following cycle, at the end of the mechanical cycle in progress.

The extraction of the parameters from the models is then done in the area designated by general reference 13 between two exclusion areas.

Of course, different detections of these phases are possible. For example, these phases can be detected by a means for analyzing the air pressure and flow in the pneumatic circuit, the analysis means then being connected to the means for acquiring pressure and flow signals in the pneumatic circuit as previously described.

However, the analysis means can also be incorporated into the assistance apparatus directly.

Likewise, the pressurization and inflation triggering phases can also be detected by an analysis means from a complementary signal delivering physiological information related to the patient's respiratory muscle activity such as, for example, a complementary surface electromyogram signal as designated by general reference 14 in FIG. 2.

This system then makes it possible to adapt the parameters for calculating the muscle pressure, i.e. to choose the model for the mechanics of the patient's passive respiratory system, to define the identification areas for the parameters of that model and the detection threshold for muscle activity.

It is then a matter of selecting, adaptively, in a set of different hierarchical models with increasing complexity, written for example in a linear form adapted to the identification of the parameters of the model, an adapted model, using the multiple linear regression method and in the least-squares sense, traditionally.

The simplest model, called the reference model, is a linear form with four parameters $P=f(V,D)=P_O+(V_O)*(V+(R_O+Rd*D)*D)$ with V and D corresponding to the air volume and flow signals as a function of time. The volume is calculated from the flow signal D by integration as a function of time. This reference model enables effective detection of the inhalation activities that trigger an inflation with a mechanical cycle-to-cycle identification of its parameters. This identification is done from air flow and volume signals corresponding to periods of die mechanical cycle not affected by the mechanical phenomena that are not described by the model and not concerned by an inhalation muscle activity that triggers an inflation. This identification is effective even when these identification areas are fixed from one patient to the next and independent of the patient's respiratory behavior. This identification area can include two disconnected parts, one during the inflation phase and the other during the exhalation phase of the mechanical cycle. Still for this reference model, a detection threshold for a fixed respiratory muscle activity between 0.5 and 2 cmH2O and preferably equal to 1 cmH2O allows effective detection of an inhalation activity that triggers an inflation.

Other models include n−k parameters with n>k and (n−k) >4 and also have linear forms f(V,D,A) with V,D and A corresponding to air volume, flow, and acceleration signals as a function of time. The acceleration is the first derivative of the flow signal D. These more complex models have the advantage of being able to describe mechanical phenomena that are not described by the reference model, such as the transition between the end of the inflation and the beginning of the exhalation of the mechanical cycle.

This ability makes it possible to propose an identification area that is no longer disconnected, but rather is continuous, both on the inflation and the exhalation. This has two advantages:

1) A simpler definition of the identification zone by excluding a period at the end of an exhalation (or just before the inflation) defined by a remote exhalation period (Dte) and a period at the beginning of the inflation defined by a proto-inflation period (Dpi); and 2) An improvement in the identification of the parameters of the models by taking into account the transition period between the inhalation and exhalation characterized by significant variations of the flow and its derivative.

Nevertheless, the increase in the complexity of the model and the extension of its ability to describe more complex mechanical phenomena may potentially cause a reduction in the sensitivity of the detection. Diagrammatically, everything occurs as if transitional phenomena related to a muscular activity are then attributed to the mechanical characteristics of the passive respiratory system.

The system according to the invention uses a method for selecting parameters for calculating the muscle pressure that makes it possible to adapt the model and the identification area for its parameters to ensure effective detection of respiratory muscle activity over the entire mechanical cycle The deteriorated performance of the identification of the respiratory muscle activity from the calculation of the muscle pressure using these more complex models can be effectively offset through an appropriate choice of the mechanical model and the identification area of the parameters of the model:

the selected model must be as close as possible to the effective mechanics of the patient's passive respiratory system;

the identification area for the parameters must be adapted to the patient's respiratory behavior so that the period of the excluded mechanical cycle is as close as possible to the period where the patient has an inhalation activity;

the threshold for detecting the respiratory activity must be adapted as a function of the adjustment quality of the chosen model and identified parameters.

The adaptation principle consists of comparing the result of the identification of the inhalation activities that trigger an inflation for a set of different models and periods (Dte and Dpi) and choosing the most suitable parameters based on three criteria:

1—the ability to ensure a correct detection of the known activities: The detection of inflations detected by an inhalation activity (Ct−(n−k)) or an inhalation activity that triggers an inflation (Ait−(n−k)) and that must be identical to the reference detection (Ct−ref).

2—the characteristics of an inhalation that triggers an inflation The selected active area is the shortest area preceding the inflations and whereof the total length (Dte+Dpi) is greater than or equal to the minimum duration of an inhalation activity considered to be significant (i.e. in the vicinity of several tenths of a second and preferably equal to 0.3 second).

3—the properties of hierarchically interlocking models: the selected model is the simplest model ensuring an adjustment over the identification area of the parameters of the measured pressure, which is statistically equivalent to the most complex model (or the model having the most parameters).

For each combination of models and identification areas, the result of the detection of a triggered inflation (Ct−(n−k)) is calculated over a period of several tens of mechanical cycles (preferably 20) and is compared to the reference result (Ct−ref). Among the combinations whereof the result can be superimposed on the reference result (Criterion 1), the combinations corresponding to the optimal exclusion area (Criterion 2) are identified and then among those combinations, the optimal model is selected (Criterion 3).

This automatic adaptation of the model makes it possible to ensure on one hand a detection of the activities that trigger an inflation that is at least as effective as the validated reference method, and on the other hand an effective detection of the other respiratory activities present during a mechanical cycle in the event the breathing activity of the patient and the assistance device are not properly adapted.

This method also has the advantage of being able to continuously monitor both the evolution of the respiratory behavior and the mechanics of the patient's respiratory system.

According to a first embodiment, the device uses the detection of the inflations triggered by the patient's inhalation by the reference model with four parameters. This embodiment has the advantage of reducing the input signals of the device to only the pressure and flow signals.

According to a second embodiment, the information on the inflation triggering mechanism is provided by an additional signal, which can be provided by the assistance apparatus or by an additional sensor. In the first case, it involves a signal representative of the opening and triggering state of the inflation valves inside the assistance apparatus. In the second case, it involves a signal representative of the patient's inhalation activity provided by a non-invasive sensor and separate from the pressure or flow signals, such as an activity detector for a muscle with an inhalation activity from a surface electromyogram (sEMG or sMMG) or movement (impedancemetry).

This automatic detecting system was experimentally tested in three situations:

i) to evaluate the selection method of the simplest adapted model (Criterion 3);

ii) to evaluate the method for optimally defining the identification areas (Criterion 2);

iii) to evaluate the combination of these models.

1) Evaluating the selection method for the simplest adapted model (criterion 3):

This study was conducted from pressure and flow recordings done on an artificial mechanical lung ventilated by an assistance apparatus having fully known mechanical characteristics. The selection method on the quality of the adjustment measured by the statistical comparison of the residue leads to the selection, as the simplest statistically equivalent model (with an alpha risk of 1% or 5%), of the minimum model necessary to describe the mechanics of the mechanical lung.

2) Evaluating the optimal definition method for the identification zones (criterion 2):

This study was conducted from old recordings done in 14 patients receiving partial breathing assistance who had suffered a properly conducted weaning failure and to that end having undergone a specific and invasive exploration of their respiratory activity through the measurement of the esophageal pressure.

In these patients, the detection ability using the Bon-invasive method is measured by the concordance between the activity detected by calculating the muscle pressure and the activity detected by reading the esophageal pressure. The value of the concordance calculated using the automatic method for selecting identification zones is compared using the Bland and Altman method at the optimal concordance observed for all possible combinations of periods that define the identification area and for a fixed complex model. An analysis of the graphic representation shows that the two methods are interchangeable with a reduced concordance with the automatic method down by 4% and an average deviation of 4%.

In these patients, the values of the optimal periods for defining the exclusion area were identified to detect activities triggering an inflation and for detecting all of the triggering or non-triggering inhalation activities. These optimal periods, and in particular the remote exhalation period (Dte), are directly related to the periods measured between the beginning of inhalation activity and the triggering of the inflation defined from the esophageal pressure.

3) Evaluation of the optimal definition method:

This study was conducted from old recordings done in 17 patients receiving partial breathing assistance having undergone a non-invasive exploration of their respiratory activity by measuring with a surface electromyogram of the diaphragm (sEMG). The detection of triggering and non-triggering inhalation activities using the automatic method is compared, using the Bland and Altman method, to that provided by the manual reading of the sEMG, Flow and Pressure signals. These two methods can be superimposed to detect the two types of inhalation activity that trigger and do not trigger an inflation.

Other embodiments of such a system can of course also be considered.

The invention claimed is:

1. A method for detecting respiratory muscle activity of a patient receiving assisted breathing from a system, which is connected to an assistance apparatus connected to the patient by a pneumatic circuit, the method comprises:
   acquiring air pressure and flow signals in the pneumatic circuit with a pressure sensor and a flow sensor,
   continuously estimating by an estimation unit, from the acquired air pressure obtained by the pressure sensor and flow signals obtained by then the flow sensor, a theoretical air pressure expected in the pneumatic circuit in absence of respiratory muscle activity from the patient,
   comparing by a comparison unit the estimated theoretical air pressure of the estimation unit and the actual acquired air pressures of the pressure sensor and flow sensor, and
   continuously detecting a pressure differential showing respiratory muscle activity in the patient based on the comparison,
   wherein the estimating step by the estimation unit comprises configuring and adapting models by a modeling unit for the patient's passive respiratory system,
   wherein the modeling by the modeling unit comprises a set of a configurable models and the estimating by the estimation unit comprises extracting input parameters for said models by an extraction unit from the measured pressure signal by the flow and pressure sensors, so as to trigger the operation of these models based on these parameters, and selecting, by a selection unit, the most discriminating model in terms of detection and non-detection of respiratory muscle activity by the patient and/or the simplest in terms of number of parameters used to make its estimate,
   wherein the extracting by the extraction unit is adapted to extract the parameters over at least one mechanical cycle made up successively of an inflation and an exhalation, excluding the pressurization phase at the beginning of the mechanical cycle in progress and the phase triggering the inflation for the following cycle at the end of the mechanical cycle in progress, and
   wherein the extracting by the extraction unit is done in an identification area that is continuous between the excluded pressurization phase at the beginning of the mechanical cycle in progress and the phase triggering the inflation for the following cycle at the end of the mechanical cycle in progress.

2. The system for detecting respiratory muscle activity of a patient receiving assisted breathing according to claim 1, wherein the modeling unit assumes the form of models depending at least on the air volume and flow circulating in the pneumatic circuit.

3. The method for detecting respiratory muscle activity of a patient receiving assisted breathing according to claim 1, wherein the pressurization phase and the phase triggering the inflation are detected by analyzing by an analyzing unit the air pressure and flow in the pneumatic circuit by a pressure sensor and a flow sensor.

4. The method for detecting respiratory muscle activity of a patient receiving assisted breathing according to claim 3, wherein the analyzing unit is connected to the pressure sensor and flow sensor.

5. The method for detecting respiratory muscle activity of a patient receiving assisted breathing according to claim 3, wherein the analyzing unit is integrated into the assistance apparatus.

6. The method for detecting respiratory muscle activity of a patient receiving assisted brething according to claim 1, wherein the pressurization and inflation triggering phases are detected by analyzing a complementary signal delivering physiological information related to the patient's respiratory muscle activity.

7. The method for detecting respiratory muscle activity of a patient receiving assisted breathing according to claim 6, wherein the complementary signal is a surface electromyogram signal.

* * * * *